United States Patent [19]

Perler

[11] Patent Number: 4,614,191
[45] Date of Patent: Sep. 30, 1986

[54] SKIN-COOLING PROBE

[76] Inventor: Robert F. Perler, 25 Lockwood Ave., New Rochelle, N.Y. 10801

[21] Appl. No.: 529,009

[22] Filed: Sep. 2, 1983

[51] Int. Cl.$^4$ .............................................. A61F 7/00
[52] U.S. Cl. ................................. 128/399; 128/24.1
[58] Field of Search .............................. 128/24.1–24.3, 128/26, 303.1, 303.13, 329 A, 381, 399–403, 639, 783, 742, 774, 781; 219/800, 803, 227

[56] References Cited

U.S. PATENT DOCUMENTS

| 3,132,688 | 5/1964 | Nowak | 128/403 |
| 3,133,539 | 5/1964 | Erdis | 128/399 |
| 3,207,159 | 9/1965 | Tateisi | 128/399 |
| 3,289,749 | 12/1966 | Crump | 128/401 |
| 3,502,080 | 3/1970 | Hirschhorn | 128/303.1 |
| 3,923,064 | 12/1975 | Lexpold | 128/329 A |
| 4,317,450 | 3/1982 | Chalmers | 128/303.13 |
| 4,440,167 | 4/1984 | Takehisa | 128/303.1 |

FOREIGN PATENT DOCUMENTS

| 672148 | 10/1963 | Canada | 128/781 |
| 364317 | 2/1973 | U.S.S.R. | 128/303.1 |
| 438422 | 1/1975 | U.S.S.R. | 128/303.13 |

Primary Examiner—Edward M. Coven
Assistant Examiner—Max F. Hindenburg
Attorney, Agent, or Firm—Handal & Morofsky

[57] ABSTRACT

A skin-cooling probe used for the purpose of anesthetizing or desnsitizing the target skin area prior to the removal of hairs by electrolysis. The probe is manipulated by one finger, is enabled by a foot pedal. A refrigerant chip is powered by electric current and operates by polarizing hot and cold via the Peltier effect. The cold side is applied to the target skin area by digital manipulation of the probe. A heat sink dissipates heat generated by the hot side of the refrigerant chip. The refrigerant chip and the finger socket are both rotatable with respect to an axis, thereby avoiding clumsiness and difficulty in applying the cold side of the refrigerant chip to the target skin area. The current to the refrigerant chip is cyclically controlled by timing circuitry, thereby defining a cooling/recovery cycle. A light signal connected to the timing circuitry signals probe readiness.

15 Claims, 5 Drawing Figures

U.S. Patent   Sep. 30, 1986   4,614,191
FIG. 1.
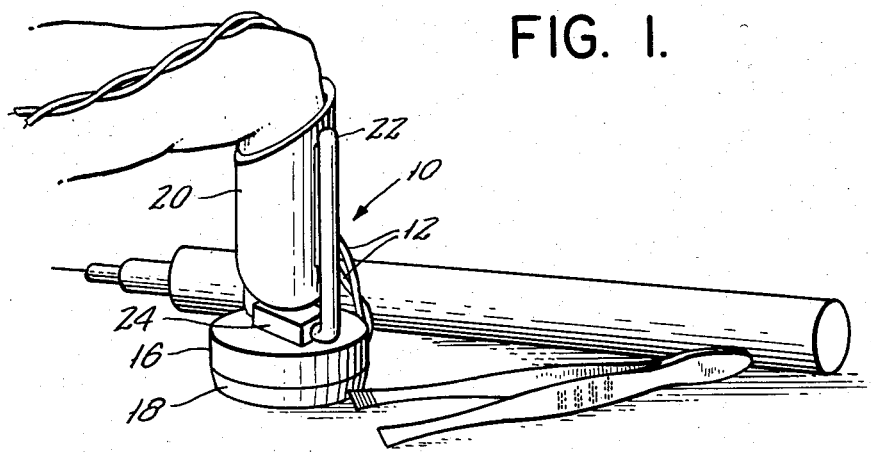
FIG. 2c.
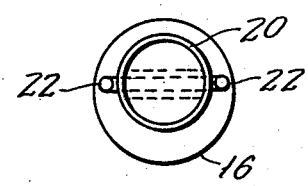
FIG. 3.
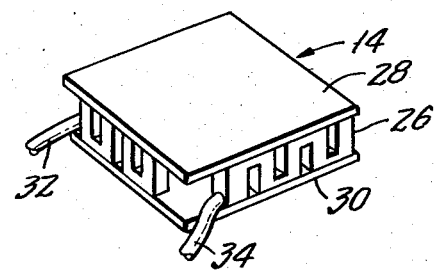
FIG. 2a.   FIG. 2b.
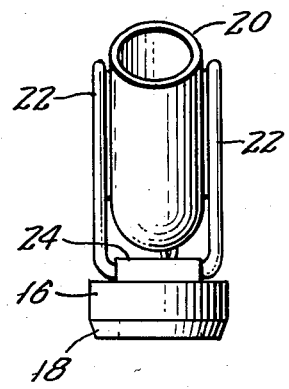 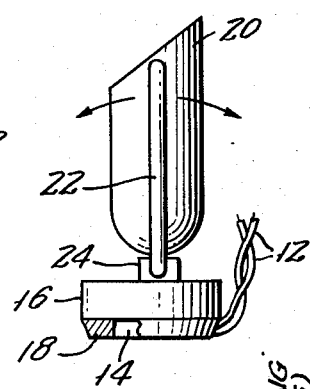
FIG. 4.
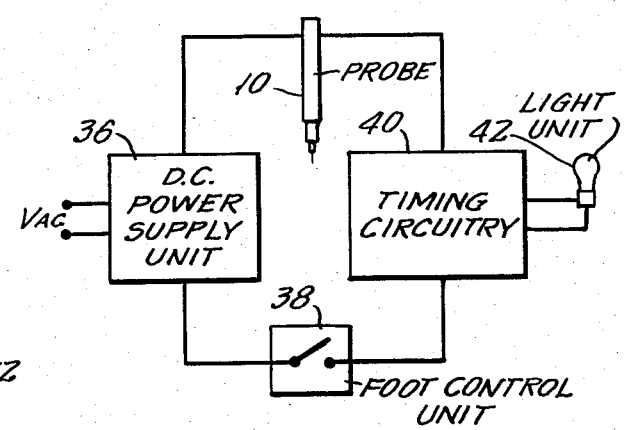
FIG. 2d.
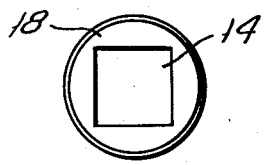
FIG. 5.
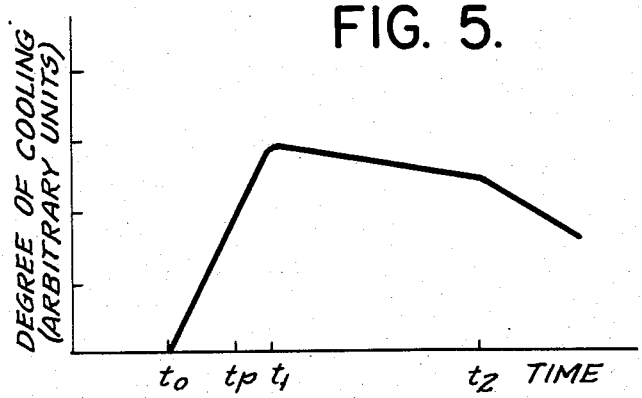

SKIN-COOLING PROBE

TECHNICAL FIELD

The invention relates to a device for anesthetizing skin prior to electrolysis.

BACKGROUND ART

Electrolysis is a medically proven method of permanently removing hair from the human body. This object is achieved by destroying hair roots with an electric current a process which is sometimes painful. Presently, no means of anesthetizing or desensitizing skin are commercially available to electrologists other than those in medicinal form.

Injections and refrigerants are not licensed for use by the electrologist. Although the application of ice to the skin will raise the threshold of pain, the heat generated by the human body causes the ice to melt. However, the water produced by this melting causes minor shocks when the electric current is applied to the skin.

The result is that a definite need exists among electrologists for a device which can raise the threshold of pain without leaving a residue on the skin, and which can be conveniently used during electrolysis.

DISCLOSURE OF INVENTION

The invention as claimed is intended to provide a remedy. It solves the problem of how to raise the threshold of pain safely and conveniently prior to electrolysis.

The skin-cooling probe according to the invention is a device which electrically produces coldness on the probe end surface. When the end surface of the probe is pressed against the subjects skin, the coldness raises the threshold of pain but leaves the surface temperature of the skin above 0° C. Thus, the application of coldness causes no cellular histological or morphological changes or damage. Upon withdrawal of the skin-cooling probe from the site of application, the skin experiences a pleasant "after-cool" feeling.

In addition to safe desensitization, the invention offers the advantage of convenient application. The skin-cooling probe is designed for application by means of a single finger. This is ideally suited for use in electrolysis because while the first hand holds the electrolysis probe and tweezers, and the middle finger and thumb of the second hand hold the skin taut, the skin-cooling probe can be applied by manipulating the index finger of the second hand.

BRIEF DESCRIPTION OF DRAWINGS

One way of carrying out the invention is described in detail below with reference to drawings which illustrate only one specific embodiment, in which:

FIG. 1 shows a side view of the skin-cooling probe in accordance with the invention with the operator's finger inserted and the tweezers and electrolysis probe used with the inventive apparatus in accordance with the inventive method;

FIGS. 2a–d shows views of the skin-cooling probe from the front, side, top and bottom, respectively;

FIG. 3 shows a perspective view of the refrigerant chip;

FIG. 4 shows a block diagram of the system according to the present invention; and FIG. 5 shows a graph of the cooling cycle of the probe.

BEST MODE FOR CARRYING OUT THE INVENTION

FIG. 1 shows the probe 10 according to the preferred embodiment with the finger inserted. The probe 10 is connected to the power supply via conducting wires 12. The wires 12 are connected to the refrigerant chip 14. Refrigerant chip 14 is rigidly fixed to the base of heat sink 16. Insulator 18 is also rigidly fixed to the base of heat sink 16, abutting the refrigerant chip 14 on all sides. Insulator 18 can be made from any material that is both thermally and electrically insulating (e.g., wax or plastic).

The operator's finger is inserted in the finger socket 20 which is thermally and electrically insulated. Finger socket 20 is a tube-like member and is rigidly fixed to the rotatable U-shaped support means, bar 22. The U-bar 22 is rotatably fixed in mount 24, which is in turn rigidly fixed to the top surface of heat sink 16. FIGS. 2a–d show front, side, top and bottom views of skin-cooling probe 10. In FIG. 2a it can be seen that each prong of the U-shaped bar 22 supports one side of the finger socket 20. The base of the U-shaped bar 22 occupies a cylindrical channel in mount 24 and is denoted by dashed lines.

FIG. 2c shows that the cross section of the heat sink 16 is circular. Of course, the shape of heat sink 16 is immaterial to the concept of the present invention and need not have a circular cross section. Heat sink 16 may be made from any material that is thermally conductive.

FIG. 2d shows that the base of the refrigerant chip 14 is square-shaped. However, the shape of the base is immaterial and need not be square.

FIG. 2b depicts the rotation of finger socket 20 and U-shaped bar 22 (which are rigidly fixed relative to each other) relative to the mount 24 and the base 16 (which are also rigidly fixed relative to each other). The rotation (depicted by the arrows) takes place about the axis of rotation denoted by A in the figure, thereby allowing one angular degree of freedom between the finger socket and base.

FIG. 3 shows a perspective view of the refrigerant chip 14 which comprises a network of p-n junctions sandwiched by ceramic plates 28 (hot) and 30 (cold). Ceramic plates 28 and 30 are thermally conductive and electrically insulating. Also shown are the chip terminals 32 and 34, which are connected to wire leads 12. The refrigerant chip depicted in FIG. 3 is well known in the art and is manufactured by Borg-Warner Thermoelectrics. Other companies produce chips with similar characteristics.

A block diagram of the system according to the present invention is presented in FIG. 4. The probe 10 is powered by dc power supply unit 36. The power supply is switched on by foot control unit 38 which comprises a foot-operated switch. Current flows in the circuit, however, only in accordance with the parameters of timing circuitry 40. The light unit 42 is connected to timing circuitry 40.

The preferred embodiment of the probe 10 operates as follows: current flows to the refrigerant chip 14 which is actually a thermoelectric module that uses the "Peltier effect" to polarize hot from cold. The heat is drawn off to a heat sink 16 by conduction. (The heat sink 16 is preferably made of copper.) The heat sink, in turn, vents the heat by radiation to the surrounding atmosphere. The rate of heat dissipation is maximized by optimizing the ratio of the heat sink surface area to the heat sink mass. The amount of heat that builds up on the heat sink is minimized by utilizing a reduced exposure time and allowing a subsequent period of recovery (i.e., cooling of the heat sink). The cold side of the refrigerant chip achieves a temperature of about 0° C. after a 10-second application. As will be made apparent in the subsequent description, at some point in time the heat generated by the hot side of the refrigerant chip 14 begins to have an effect on the cold side by raising its temperature. To optimize the power used, timing circuitry 40 controls the current supplied to probe 10, thereby defining a 28-second cooling/recovery cycle in the preferred embodiment. The cold plate 30 of the refrigerant chip 14 is applied to the patient's skin during the cooling period and removed during the recovery period (i.e., the period during which the current is off and the heat sink 16 cools).

The convenience afforded by the present invention lies in the fact that the probe 10 can be applied by movements of one finger. In order to achieve the anesthetizing effect, the ceramic plate 30 of refrigerant chip 14 must be pressed against the target skin surface area. Because the probe operator holds the electrolysis probe and tweezers in the first hand and holds the target skin surface taut with the second hand during the electrolysis operation, it is especially convenient to be able to apply the skin cooling probe by means of the free index finger on the second hand. To avoid clumsiness and difficulty in this operation, the probe 10 is designed to achieve a pivot swivel effect. When the operator places the probe 10 against the target skin surface area by means of finger movements, the mount-heat sink unit swivels about axis A until the bottom surface of refrigeration chip 14 lies flat against the skin surface. This free swiveling action of the mount-heat sink unit eliminates the need for any manual adjustments other than the simple movements of the operator's index finger while inserted in the finger socket 20.

The skin-cooling probe according to the present invention is switched on by means of foot control unit 38, which comprises a switch controlled by a foot pedal (not shown). Pushing the foot pedal down at time $t_o$ initiates the cooling/recovery cycle. The switch is closed and dc power supply unit 36 is enabled. Such a unit is well known in the art and comprises a transformer, a rectifier, a filter, and an adjustable feedback circuit amplifier. This dc power supply unit transforms and rectifies ac line current into low-voltage dc current. The filtered current is then fed to the feedback circuit amplifier. By adjusting this amplifier, the output of dc power supply unit 36 can be regulated to meet the specific requirements of the refrigerant chip being used.

The cooling/recovery cyle is determined by the parameters of the timing circuitry 40. A typical cooling/recovery cycle, as mentioned earlier, is 28 seconds long. The degree of cooling versus time over the course of one cycle is depicted in FIG. 5. When the foot pedal is pushed down at time $t_o$, the device is turned on. The ceramic plate 30 of refrigerated chip 14 is cooled until the time $t_1$, at which the limit of the ability of heat sink 16 to dissipate heat is reached and the hot side of refrigerant chip 14 begins to heat the cold side (i.e., ceramic plate 30). The probe is primed during the time span from $t_o$ to $t_p$ shown in FIG. 5, wherein $t_p - t_o = 2$ seconds. At time $t_p$ light unit 42 is turned on, indicating that the probe is ready for application (i.e., sufficiently cooled). The time span from $t_p$ to $t_1$ is the reaction time (i.e., due to the finite duration of human reflexes, the operator will apply the probe a certain amount of time after readiness has been signalled). Thus, at time $t_1$ (the time corresponding to maximum coldness), the operator applies the probe to the target skin area of the patient. (It will be noted that the time span from $t_0$ to $t_1$ is on the order of 3 seconds.)

The time span from $t_1$ to $t_2$ is the application period during which the target skin area is cooled. This application period is predetermined in accordance with the timing circuitry 40. The timing circuitry is suitably designed to achieve a time span $t_2-t_1$ on the order of 10 seconds. At time $t_2$ the timing circuitry 40 switches off the current to probe 10 and light unit 42, turning off both. The probe remains disabled for a recovery period of predetermined duration (on the order of 15 seconds). During this time, the circuitry 40 prevents the reactivation of probe 10. This recovery period allows time for the heat sink to cool. Only at the end of the 28-second cycle will it be possible for the operator to initiate a new cycle by pushing on the foot pedal of foot control unit 38.

Thus, during the application from $t_1$ to $t_2$ (see FIG. 5), the target skin area experiences a protopathic sensation as a result of the cooling effect of the probe. During the subsequent recovery period, when electrolysis is performed by the operator, the epicritic pain produced by removal of a hair is masked by the continued protopathic sensation resulting from the earlier application of coldness by means of the probe according to the preferred embodiment.

It will be noted that the skin-cooling probe according to the present invention is not limited in use to merely electrolysis, but rather may be used in any field where dermatological anesthetizing or desensitizing is called for (e.g., chiropractics, acupuncture, minor cosmetic surgery).

In addition, it will be noted that the preferred embodiment of the present invention has been described only for the purposes of illustration and is in no way intended to limit the scope of the claimed invention. For example, it will be obvious to one skilled in the art that the present invention can be rendered more efficient by water cooling the heat sink in order to maintain the heat sink at its ambient temperature. Also, it will be obvious to one skilled in the art that the heat sink can have a finned design whereby the fins enhance the dissipation of heat through radiation by increasing the amount of heat sink surface area exposed to the surrounding atmosphere. Naturally, under these circumstances, the exemplary 28-second cooling/recovery cycle will not be applicable.

I claim:
1. A skin-cooling probe, comprising:
(a) support means for performing a supporting function;
(b) a finger socket comprising a tube-like member, rigidly fixed to said support means at a point on said support means and adapted to receive the index finger of an operator;
(c) heat dissipation means for dissipating heat, said heat dissipation means having a base;
(d) mounting means rotably attaching said support means with only one angular degree of freedom at a point on said heat dissipation means opposite the base of said heat dissipation means;

(e) cooling means rigidly fixed to the base of said heat dissipation means, said finger socket being rotable relative to said cooling means with only one angular degree of freedom to allow manipulation of said cooling means by said index finger and the pulling taut of skin by the thumb and middle finger of said one hand, whereby the other hand of the operator is free to use a tweezer and electrolysis probe and perform electrolysis without the picking up and putting down of instruments; and (f) power supply means coupled to said cooling means.

2. A skin-cooling probe as in claim 1, wherein said cooling means comprises a refrigerant chip.

3. A skin-cooling probe as in claim 2, wherein said refrigerant chip comprises parallel plates made of thermally conducting and electrically insulating material.

4. A skin-cooling probe as in claim 1, wherein said heat dissipation means comprises a metal heat sink.

5. A skin-cooling probe as in claim 4 wherein said heat sink is finned.

6. A skin-cooling probe as in claim 4, further comprising water circulation means, wherein said water circulation means enable the water cooling of said heat sink.

7. A skin-cooling probe as in claim 1, further comprising timing circuitry means and light signalling means wherein said light signalling means are switched on by said timing circuitry means at a first predetermined time and switched off by said timing circuitry means at a second predetermined time, and said cooling means are switched off by said timing circuitry means at said second predetermined time.

8. A skin-cooling probe as in claim 7, wherein said timing circuitry means disables said cooling means until a third predetermined time.

9. A skin-cooling probe as in claim 1, wherein said finger socket is made of electrically insulating and thermally insulating material.

10. A skin-cooling probe as in claim 1, wherein said cooling means is secured to and overlies only a portion of said base and further comprising an insulator made of electrically insulating and thermally insulating material, wherein said insulator confronts and is secured to that portion of the base of said heat dissipation means not confronted by said cooling means.

11. A skin-cooling probe as in claim 1, wheren said socket further comprises closure means at one end of said cylindrical sidewalls.

12. A skin-cooling probe as in claim 11, wherein the other end of said sidewalls terminates in a n asymetrical taper.

13. A skin-cooling probe as in claim 1, wherein said mounting means allows only angular movement along parallel axes.

14. An electrolysis method for removing hair from the human body, comprising:

(a) equiping the index finger of one hand of an operator with a cooling device by inserting the index finger of said one hand into a socket supporting said cooling device;

(b) holding an area of skin having a hair to be removed from it taut using the middle finger and thumb of said one hand to provide an effective surface for cooling;

(c) applying said cooling device to the immediate area of skin surrounding said hair to be removed to anesthetize said area to reduce the ability of said area of skin to sense pain;

(d) equiping the other hand of the operator with an electrolysis probe and tweezers; and (e) using said electrolysis probe and tweezers to remove said hair while said skin is being held taut and is anesthetized.

15. Apparatus for skin-cooling and electrolysis without the picking up and putting down of instruments, comprising:

(a) support means for performing a supporting function;

(b) a finger socket comprising a tube-like member rigidly fixed to said support means at a point on said support means and adapted to receive the index finger of an operator;

(c) heat dissipation means for dissipating heat, said heat dissipation means having a base;

(d) mounting means rotably attaching said support means to said heat dissipation means with only one angular degree of freedom at a point on said heat dissipation means opposite the base of said heat dissipation means;

(e) cooling means rigidly fixed to the base of said heat dissipation means, said finger socket being rotable relative to said cooling means to allow manipulation of said cooling means with only one angular degree of freedom by said index finger and the pulling taut of skin by the thumb and middle finger of said one hand, whereby the other hand of the operator is free to use a tweezer and electrolysis probe and perform electrolysis without the picking up and putting down of instruments;

(g) an electrolysis probe; and (h) tweezers, said tweezers and probe adapted to be held in the other hand of the operator, whereby the operator may perform electrolysis without picking up and putting down instruments.

* * * * *